United States Patent [19]

Taylor

[11] Patent Number: 5,659,896
[45] Date of Patent: Aug. 26, 1997

[54] REMOVABLE WASHABLE COVER FOR VISOR

[76] Inventor: Nellie F. Taylor, 7813 E. San Carlos, Scottsdale, Ariz. 85258

[21] Appl. No.: 533,693

[22] Filed: Sep. 26, 1995

[51] Int. Cl.⁶ .................................................. A61F 9/00
[52] U.S. Cl. .................................. 2/12; 2/171; 2/209.13; 206/8; 223/84
[58] Field of Search ............................. 2/12, 15, 63, 171, 2/171.1, 175.1, 181, 181.4, 195.1, 209.11, 209.12, 209.13; 206/8; 223/24, 84

[56] References Cited

U.S. PATENT DOCUMENTS 2,655,256  10/1953  Guest ............................................ 223/84
3,029,439   4/1962  Yeschick ........................................ 2/12
5,012,531   5/1991  Schoonover ................................. 206/8
5,163,589  11/1992  Biehl ........................................... 223/24

FOREIGN PATENT DOCUMENTS 736700  11/1932  France ..................................... 2/195.1

*Primary Examiner*—Diana Biefeld
*Attorney, Agent, or Firm*—Tod R. Nissle, P.C.

[57] ABSTRACT

An improved visor includes a C-shaped band which fits around the head of the user and includes a brim attached to the band. A pliable cloth sleeve is provided which removably fits over the visor. The sleeve is removed for washing when soiled.

10 Claims, 4 Drawing Sheets

REMOVABLE WASHABLE COVER FOR VISOR

This invention relates to head wear.

More particularly, the invention relates to a visor which has a cloth surface.

Visors are well known in the art. See, for example, U.S. Pat. No. 4,023,212 to Huffman, U.S. Pat. No. 5,003,639 to White, U.S. Pat. No. 5,070,545 to Tapia, U.S. Pat. No. 5,091,995 to Oates, U.S. Pat. No. 5,107,548 to Dotzenrod, U.S. Pat. No. 5,177,810 to Minton et al., U.S. Pat. No. 5,197,150 to Bedient, U.S. Pat. No. 5,271,099 to Lin, and U.S. Pat. No. 5,373,586 to Brosnan.

A visor ordinarily comprises a resilient, C-shaped plastic band which fits around and engages a portion of the circumference of the head of a user. The band ordinarily extends over the forehead and the sides of the user's head above the user's ears. Since the band is resilient, the ends of the band are ordinarily, but not necessarily, resiliently spread apart from their normal position when the band is worn on the user's head. After the ends of the band are spread apart, they attempt to return to their normal position and press against the sides of the user's head. The pressure of the ends of the band against the user's head helps maintain the visor in position on the head. A visor can, if desired, include a band which extend completely around the head of user like the band of a baseball cap.

A brim is attached to and extends outwardly away from the band and the forehead of the user when the visor is worn. The brim functions to shade the face of the user from the sun. The visor ordinarily does not cover the top of the user's head. A baseball cap and most other hats do, in contrast, cover the top of the user's head when worn. The visor and C-shaped band are typically made from a hard, resilient plastic, but can be constructed from any desired material.

Cloth is glued or otherwise permanently affixed to the C-shaped band and brim.

A particular problem encountered during use of the visor is that the cloth covering the visor becomes soiled. This is particularly the case with the cloth which covers the inside of the C-shaped band and which presses against the user's head. Attempting to wash the visor by hand is difficult. Putting the visor in a washing machine is not desirable because the forces generated on the visor by the washing machine may cause the brim or band to break, particularly when the brim or band are constructed of plastic. As a result, when the cloth clover on a visor become dirty, it often times cannot be conveniently cleaned without damaging the visor and, the visor is simply discarded.

Accordingly, it would be highly desirable to provide an improved visor which could be readily thoroughly cleaned while minimizing the likelihood that the visor would be broken.

Therefore, it is a principal object of the invention to provide an improved visor and method for cleaning the visor.

Another object of the invention is to provide an improved visor of the type including a C-shaped head band, a brim attach to the band, and cloth covering the brim and head band.

A further object of the invention is to provide an improved visor of the type described which facilitates cleaning the cloth cover when soiled.

Still another object of the invention is to provide a method for cleaning a visor of the type described which reduces the risk that the visor will be broken or damaged during the cleaning process.

These and other, further and more specific objects and advantages of the invention will be apparent to those skilled in the art from the following detailed description thereof, taken in conjunction with the drawings, in which.

Briefly, in accordance with my invention, I provide an improved visor. The visor includes a resilient C-shaped band shaped and dimensioned to extend over the forehead and over the sides of the head of a user, and includes a brim attached to and extending outwardly from the C-shaped band to shield the face of the user from light when the visor is worn on the head of a user. A pliable C-shaped sleeve is included with the visor. The sleeve is shaped and dimensioned to be removably slid over and secured on the band and brim of the visor.

In another embodiment of my invention, I provide an improved visor. The visor includes a resilient C-shaped band shaped and dimensioned to extend over the forehead and over the sides of the head of a user and having a pair of opposing end normally each positioned against a side of the user's head when the visor is worn, and includes a brim attached to and extending outwardly from the C-shaped band to shield the face of the user from light when the visor is worn on the head of a user. A C-shaped cover is provided with the visor to facilitate cleaning of the visor when soiled. The C-shaped cover is shaped and dimensioned to removably engage each of the end of the band and extend from end of the band over the brim and the band.

In a further embodiment of the invention, I provide an improved method for cleaning a visor. The visor includes a resilient C-shaped band shaped and dimensioned to extend over the forehead and over the sides of the head of a user and having a pair of opposing end normally each positioned against a side of the user's head when the visor is worn, and includes a brim attached to and extending outwardly from the C-shaped band to shield the face of the user from light when the visor is worn on the head of a user. The method includes the steps of removably mounting on the visor a pliable C-shaped cover; removing the cover from the visor when soiled; washing the cover; and, removably mounting the cleaned C-shaped cover on the visor.

Figure 1:
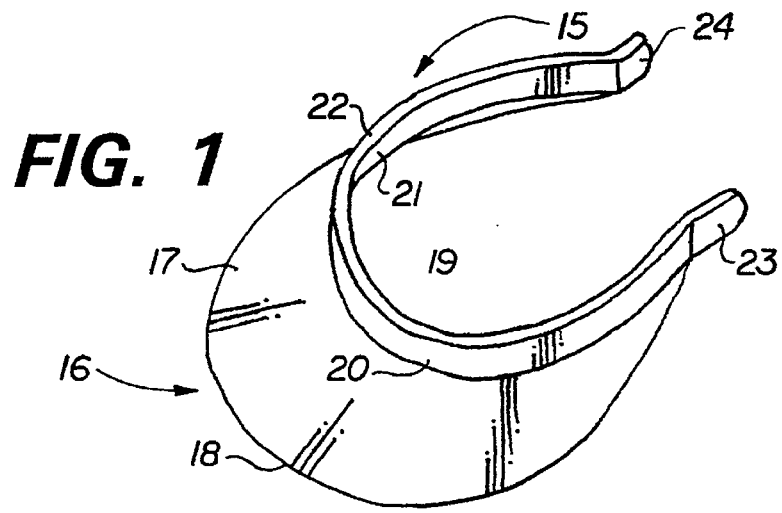
FIG. 1 is a perspective view illustrating a visor with a C-shaped head band and a brim attached to the head band.
Figure 2:
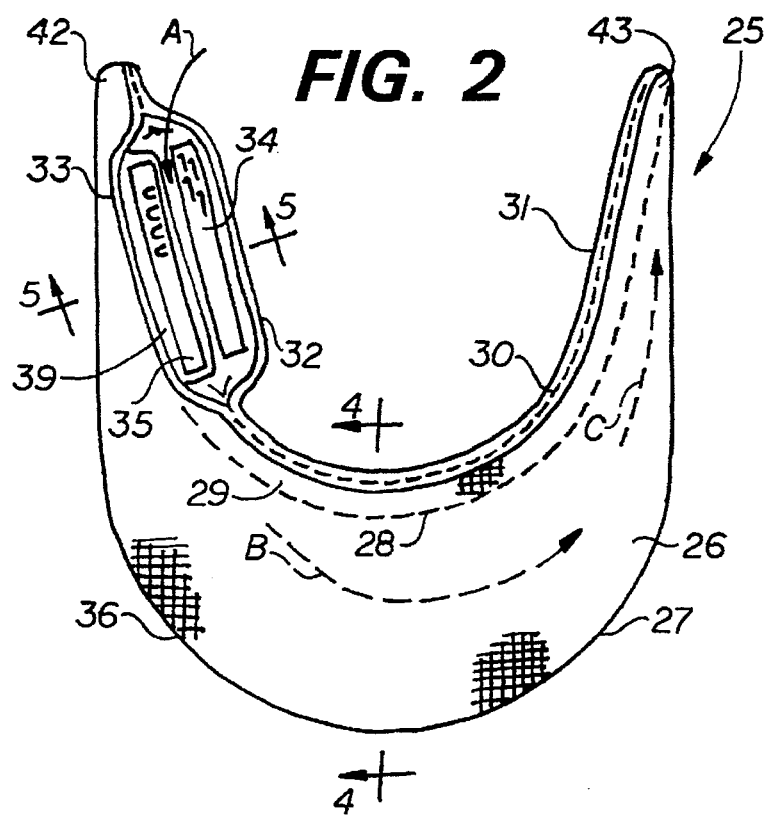
FIG. 2 is a top view illustrating a pliable cloth visor sleeve or cover constructed in accordance with the principles of the invention to be removably slid over and tensioned and secured on the visor of FIG. 1.
Figure 3:
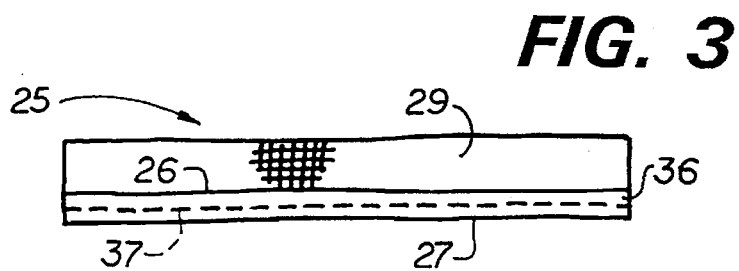
FIG. 3 is a front view further illustrating the cloth sleeve of FIG. 2.
Figure 4:
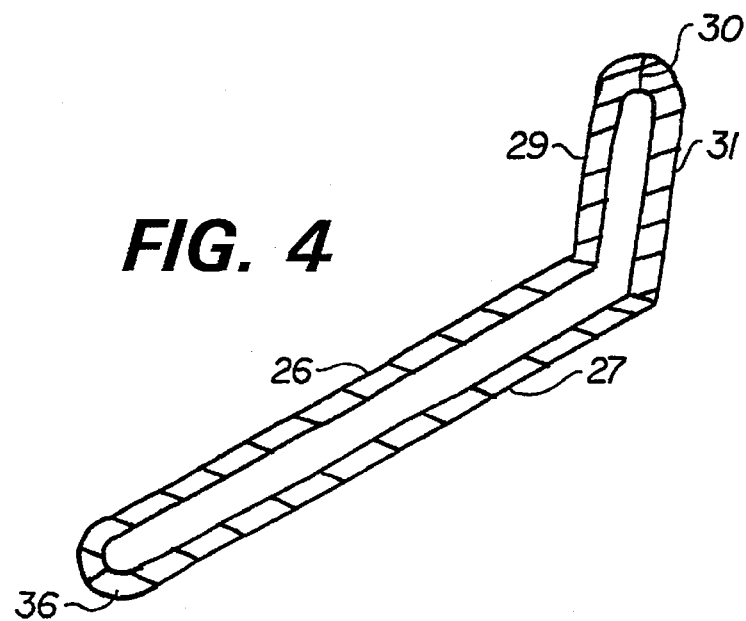
FIG. 4 is a section view of the cloth sleeve of FIG. 2 further illustrating the construction thereof and taken along section line 4—4.
Figure 5:
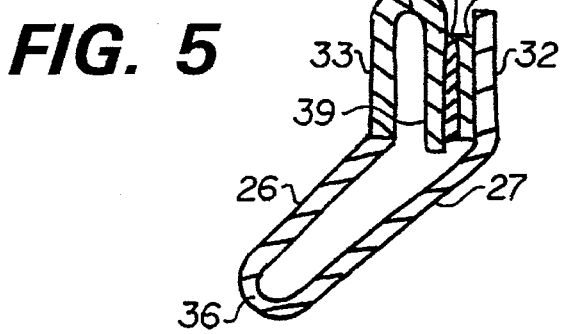
FIG. 5 is a section view of the cloth sleeve of FIG. 2 illustrating the construction of the opening in the sleeve which permits the visor of FIG. 1 to be slid into the sleeve and taken along section line 5—5 thereof.

Turning now to the drawings, which depict the presently preferred embodiments of the invention for the purpose of illustrating the practice thereof and not by way of limitation, and in which like reference characters refer to corresponding elements throughout the several views, FIG. 1 illustrates a visor 15 including a C-shaped band 19 and a brim 16. Band 19 normally is resilient, is shaped and dimensioned to conform to and extend over the forehead and sides of the head of a user, and is made from a hard, substantially rigid plastic. When the visor 15 is mounted on the head of a user, band 19 flexes so that the opposed, spaced apart ends 23 and 24 are forced apart by the head of the user, i.e., the user's head has a width greater than the normal distance between ends 23 and 24 illustrated in FIG. 1. Band 19 includes inner arcuate surface 21, outer arcuate surface 20, and upper edge or lip 22. Brim 16 includes upper arcuate surface 17 and outer edge 18. Visor 15 can be fabricated from any desired material, but ordinarily is produced from a substantially rigid, but resilient, material.

A pliable C-shaped sleeve 25 to cover visor 15 is illustrated in FIGS. 2 to 5. The sleeve 25 includes a brim covering segment including an upper C-shaped cloth section 26 attached to a lower C-shaped cloth section 27 by a stitch line 37. Sections 26 and 27 generally have the same shape and dimension. The sleeve 25 also includes a ridge portion for covering the C-shaped band 19. The ridge portion includes a front cloth section 29 attached to cloth section 26 by a stitch line 28. The ridge portion also includes an inner cloth section 31 attached to cloth section 29 by a stitch line 30. Section 31 is also attached to section 27.

Stitched together cloth sections 26, 27, 31, and 29 enclose and bound a C-shaped inner area which generally corresponds in shape and dimension to visor 15. The C-shaped inner area is accessed only by opening cloth portions 32 and 33 in the manner shown in FIG. 2.

Cloth section 31 includes a portion 32 having a strip 34 of "hook" VELCRO (Trademark) fastener material secured to the inner surface of portion 32. Cloth section 29 includes a portion 33 having a flap 39 attached thereto and pivotable along a stitch line 30. A strip 35 of "loop" VELCRO (Trademark) fastener material is secured to flap the inner surface of portion 33. Strips 35 and 34 normally oppose one another. When strips 34 and 35 are pulled and spaced apart in the manner shown in FIG. 2, then one end 23 of visor 15 is slid into sleeve 25 by inserting end 23 between portions 32 and 33 and between strips 34 and 35 in the manner illustrated in FIG. 6. Strips 34 and 35 and portions 32 and 33 bound and define an opening in sleeve 25. If desired, instead of the opening defines by strips 34 and 35 and portions 32 and 33, another opening or openings can be formed in sleeve 25 at any other location(s) to facilitate mounting sleeve 25 on visor 15.

Figure 6:
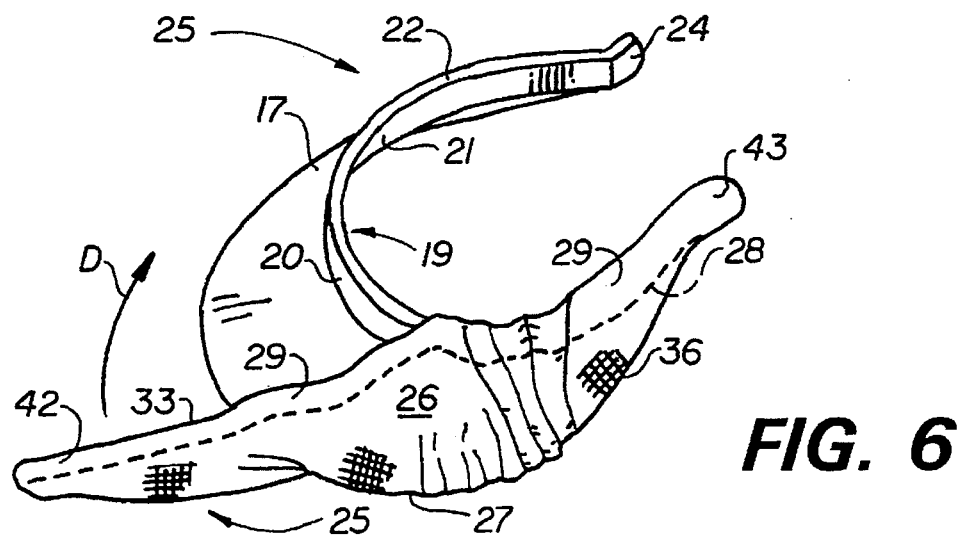
FIG. 6 is a perspective view illustrating the pliable sleeve of FIGS. 2 to 5 after one end of the visor band is lid through the opening of the sleeve and installation of the sleeve over the visor is begun.
Figure 7:
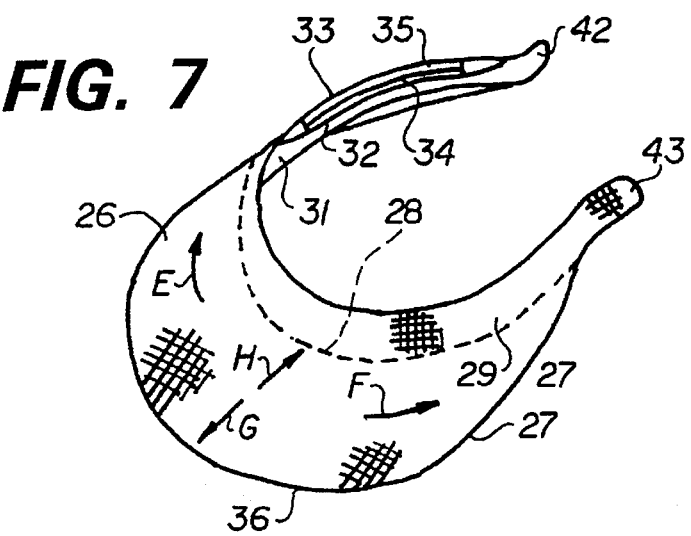
FIG. 7 is a perspective view illustrating the pliable sleeve of FIGS. 2 to 5 after it is completely installed over the visor and the opposing Velcro strips in the sleeve opening are pressed together to close the sleeve opening.
Figure 8:
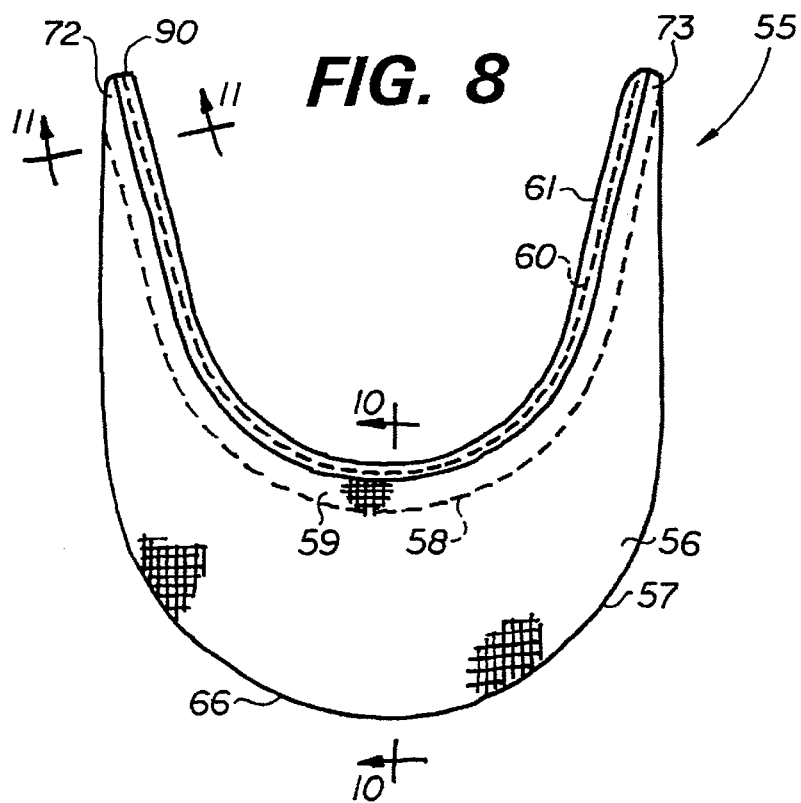
FIG. 8 is a top view illustrating a pliable visor cover constructed in accordance with an alternate embodiment of the invention.
Figure 9:
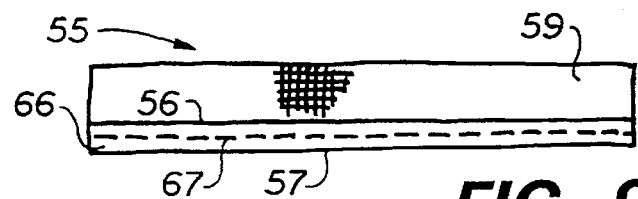
FIG. 9 is a front view further illustrating the visor cover of FIG. 8.

After sleeve 25 is partially pulled onto visor 15 in the manner shown in FIG. 6, the remainder of sleeve 25 is slid over the exposed portion of visor 25 in FIG. 6, including over end 34, and strips 34 and 35 are pressed together to produce the configuration illustrated in FIG. 7. In FIG. 7, cloth pocket 42 fits over and conforms to end 24, and cloth pocket 23 fits over and conforms to end 43. Sleeve 25 completely covers visor 15 in FIG. 7. When desired, sleeve 25 is removed from visor 15 by separating strips 34 and 35 and pulling end 24 and the remainder of visor 15 out through the opening or mouth formed by opposing portions 32 and 33. Sleeve 25 is preferably sized such that when it is installed on visor 15 in the manner shown in FIG. 7, the cloth or other material comprising sleeve 25 is tensioned such that the cloth smoothly and tautly conforms to the contours of at least some, preferably all, of the portions of visor 15, particularly the upper surface 17 of the brim of the visor. Typically, cloth in sleeve 25 positioned over and contacting surface 17 is tensioned in the directions indicated by arrows E, F, G, and H in FIG. 7.

An alternate embodiment of a visor cover utilized in the practice of the invention is illustrated in FIGS. 8 to 11. The visor cover 55 includes a brim segment including an upper C-shaped cloth section 56 attached to a lower C-shaped lip section 57 by a stitch line 66. Section 57 can, if desired, comprise an elasticized cloth strip or an elasticized "bias tape" strip. The brim segment covers the upper surface 17 and edge 18 of a visor 15. The visor cover 55 also includes a ridge portion for covering the C-shaped band 19. The ridge portion includes a front cloth section 59 attached to an inner lip section 61 by a stitch line 60. Cloth pockets 72 and 73 are formed at the distal ends of sections 56 and 59. Pocket 72 is shaped and dimensioned to conform to and fit over end 24 of visor 15. Pocket 73 is shaped and dimensioned to conform to and fit over end 23 of visor 15. Lip section 61 is shaped to fit over the upper edge 22 of band 19. Lip section 57 is shaped and dimensioned to fit over and conform to the C-shaped edge 18 of brim 16 of a visor 15.

Figure 10:
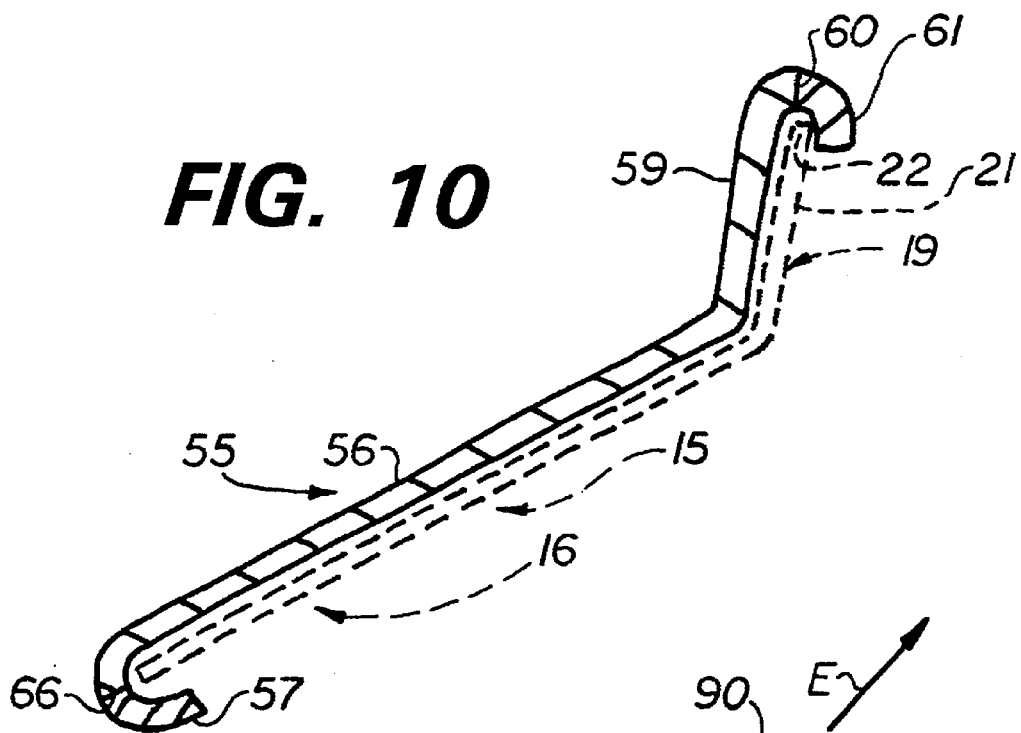
FIG. 10 is a section view of the cover of FIG. 8 further illustrating construction details thereof and taken along section line 10—10 thereof; and, FIG. 11 is a section view illustrating one of the pockets on the pliable brim cover of FIG. 6.
Figure 11:
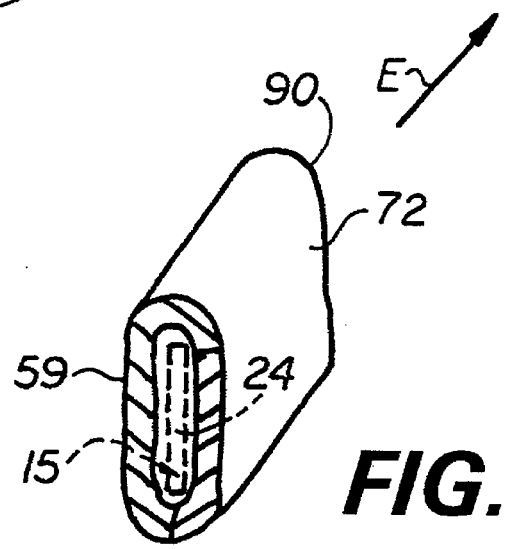

To install cover 55 on a visor 15, pocket 42 is slipped over end 24, pocket 73 is slipped over end 23, lip section 61 is fit over C-shaped upper edge 22, and lip section 57 is fit over C-shaped edge 18 of brim 16 of a visor 15 in the manner illustrated in FIGS. 10 and 11. The back 90 of pocket 72 is enclosed or stitched such that end 24 cannot slip out through pocket 72 in the direction of arrow E. The backs of each of pockets 73, 42 and 43 are similarly closed or stitched together. Pockets 72 and 73 completely cover ends 24 and 23, respectively, when cover 55 is installed on a visor 15. As shown in FIG. 10, however, cover 55 does not completely cover the underside of brim 16 nor the inner surface 21 of C-shaped band 19.

Both the cover 55 and the sleeve 25 are preferably shaped and dimensioned such that each snugly and tautly fits over a visor 15.

In use, sleeve 25 and cover 55 are each mounted on a separate visor 15 in the manner described. When soiled, sleeve 25 and cover 55 are removed from visor 15 and are washed or otherwise cleaned. The cleaned sleeve 25 and cover 55 are then remounted on their respective visor 15.

Having described my invention in such terms as to enable those skilled in the art to understand and practice it, and having identified the presently preferred embodiments thereof, I claim:

1. A combination visor and visor cover, said visor including
    a resilient C-shaped band shaped and dimensioned to extend over the forehead and over the sides of the head of a user without covering the top of the head of a user, the band having a pair of opposing spaced apart ends normally each positioned against a different one of the sides of a user's head when the visor is worn, and
    a brim attached to and extending outwardly from the C-shaped band to shield the face of a user from light when the visor is worn on the head of a user,
  said cover comprising a pliable C-shaped sleeve
    (a) shaped and dimensioned to be removably pulled over and conform to and replicate the shape of said band and said brim;

(b) including a pair of pockets each shaped to fit over and conform to a different one of said ends of said band; and, (c) which maybe worn with said visor such that a portion of each of said pockets contacts the head of a user.

2. The combination of claim 1 wherein said sleeve completely covers and conforms to and replicates the shape of said brim and said band.

3. The combination of claim 1 wherein said sleeve is washable.

4. The combination of claim 1 including an opening in said sleeve through which said visor can be slipped out of said cover.

5. The combination of claim 4 wherein said opening is located adjacent said band when said cover is installed on said visor.

6. A combination visor and visor cover, said visor including a brim to shield the face of a user from light when the visor is worn on the head of a user, and a resilient C-shaped band attached to and extending outwardly from and at an angle to said brim and shaped and dimensioned to extend over the forehead and over the sides of the head of a user, the band having a pair of opposing spaced apart ends normally each positioned against a different one of the sides of a user's head when the visor is worn, said cover comprising a pliable C-shaped sleeve (a) shaped and dimensioned to be removably pulled over and tautly conform to said band and said brim;

(b) including a pair of pockets each shaped to fit over and conform to a different one of said ends of said band;

(c) including a portion
- (i) located over and contacting said brim,
- (ii) tensioned in a first pair of opposing directions each generally parallel to said C-shaped band, and
- (iii) tensioned in a second pair of opposing directions each generally perpendicular to said first pair of opposing directions; and (d) which maybe worn with said visor such that a portion of each of said pockets contacts the head of a user.

7. The combination of claim 6 wherein said sleeve completely covers and conforms to and replicates the shape of said brim and said band.

8. The combination of claim 6 wherein said sleeve is washable.

9. The combination of claim 6 including an opening in said sleeve through which said visor can be slipped out of said cover.

10. The combination of claim 9 wherein said opening is located adjacent said band when said cover is installed on said visor.

* * * * *